United States Patent [19]

Koyama et al.

[11] Patent Number: 5,591,711
[45] Date of Patent: Jan. 7, 1997

[54] L-LYSYL-GLYCYL-L-HISTIDINE AND THERAPEUTIC AGENT FOR WOUND HEALING CONTAINING THE SAME

[75] Inventors: Masayoshi Koyama; Mikiko Takahashi; Masayoshi Yanagawa, all of Saitama, Japan

[73] Assignee: Hoechst Japan Limited, Tokyo, Japan

[21] Appl. No.: 444,845

[22] Filed: May 19, 1995

[30] Foreign Application Priority Data

May 27, 1994 [JP] Japan ..................... 6-115161

[51] Int. Cl.$^6$ ............................. C07K 5/09; A61K 38/06
[52] U.S. Cl. .................. 514/6; 514/18; 530/331
[58] Field of Search ................... 530/331; 514/6, 514/18

[56] References Cited

U.S. PATENT DOCUMENTS

| | | | |
|---|---|---|---|
| 4,760,051 | 7/1988 | Pickart | 514/6 |
| 5,023,237 | 6/1991 | Pickart | 514/18 |
| 5,118,665 | 6/1992 | Pickart | 514/6 |
| 5,164,367 | 11/1992 | Pickart | 514/6 |
| 5,386,012 | 1/1995 | Strid | 530/331 |

FOREIGN PATENT DOCUMENTS

| | | |
|---|---|---|
| 5-501253 | 3/1993 | Japan . |
| 88/08851 | 11/1988 | WIPO . |
| 91/03488 | 3/1991 | WIPO . |
| 9107431 | 5/1991 | WIPO . |

OTHER PUBLICATIONS

Dijke et al., "Growth Factors For Wound Healing", *Bio/Technology*, vol. 7:793–799, (1989).
Pickart et al., "Biological Activity Of Human Plasma Copper–Binding Growth Facor Glycyl–L–histidyl–L–lysine", *Methods In Enzymology*, vol. 147:314–328, (1987).
Pickart, "The Use Of Glycylhistidyllysine In Culture Systems", In Vitro, vol. 17, No. 6, pp. 459–466, (1981).
Audhya et al., "Tripeptide Structure of Bursin, A Selective B–Cell–Differentiating Hormone of The Bursa of Fabricius", *Science*, vol. 231:997–999, (1986).
Lote et al., "An Inhibitory Tripeptide From Cat Spinal Cord", *Nature*, vol. 264:188–189, (1976).
Runyan et al. "The Journal of Cell Biology", vol. 125, No. 4, May, 1994 pp. 928–943.

Primary Examiner—Howard E. Schain
Attorney, Agent, or Firm—Foley & Lardner

[57] ABSTRACT

L-lysyl-glycyl-histidine and metal complexes thereof, for example, L-lysyl-glycyl-L-histidine: copper (II).

The L-lysyl-glycyl-L-histidine and salt thereof have a fibroblast proliferation promoting activity and then it is useful as a wound healing agent.

11 Claims, No Drawings

L-LYSYL-GLYCYL-L-HISTIDINE AND THERAPEUTIC AGENT FOR WOUND HEALING CONTAINING THE SAME

BACKGROUND OF THE INVENTION

1. Field of the Invention

This invention relates to a new tripeptide having an amino acid sequence L-lysyl-glycyl-L-histidine and/or metal complexes thereof, and a pharmaceutical composition for wound healing containing the same as an active ingredient.

2. Description of the Prior Art

Various growth factors are known to be involved in the process of wound healing (Dijke et al., Biotechnology, Vol. 7, p. 793–798, 1989). TGF-β (transforming growth factor-β) and PDGF (platelet-derived growth factor), in particular, are known to proliferate fibroblasts, induce the cells to a damaged site and enhance wound repairing.

Some tripeptides and metal complexes thereof have been known to have a cell proliferation effect. For example, glycyl-L-histidyl-L-lysine, which was isolated from plasma or synthesized and metal complexes thereof, such as, glycyl-L-histidyl-L-lysine: copper (II) are involved in cell proliferation of hepatocytes, neurocytes, kidney cells, thyroid cells, etc., and maintenance of growth (Picart, L. Method, Enzym. Vol. 147, p. 314–328, 1987; Picart, L. IN Vitro, Vol. 17, p. 459–466, 1981; Picart, L. U.S. Pat. No. 4,760,051 ). It is assumed that the cell proliferation activity of glycyl-L-histidyl-L-lysine involves binding of an essential metal ion of trace elements such as copper ion and incorporating the copper ion in cells (Picart, L. IN Vitro, Vol. 17, p. 459–466, 1981). Also disclosed is a use of glycyl-L-histidyl-L-lysine and metal complexes thereof, for example, glycyl-L-histidyl-L-lysine: copper (II) as an agent for promoting a therapy of affected bones and other hard tissues such as cartilage of warm-blooded animals (Picart, L. R., Japanese Patent Publication No. Hei 5-501253).

L-lysil-L-histidyl-glycine was isolated from an avian bursa fabricii as a B cell differentiating hormone (Audhya, T. et al. Science Vol. 231, p. 997–999, 1986). Also it is disclosed that L-lysyl-L-histidyl-glycine is used as an agent for promoting a therapy for the affected bones and other hard tissues such as cartilage (Picart, L. R., the above-mentioned Patent Publication).

L-histidyl-glycyl-L-lysine and L-histidyl-L-lysyl-glycine have been isolated from the feline spinal marrow as an inhibitor of transmission of neurocytes (Lore, C. J. et al., Nature, Vol. 264, p. 188–189, 1976). On the other hand, only glycyl-L-histidyl-lysine is known to constitute a metal complex with a metal ion, for example, copper ion among the above-mentioned tripeptides (Picart, L., the afore-mentioned).

However, it has never been reported that L-lysyl-glycyl-L-histidine nor metal complexes thereof, for example, L-lysyl-glycyl-L-histidine copper (II) proliferates fibroblasts or is effective for wound healing.

SUMMARY OF THE INVENTION

Consequently, an object of the invention is to provide a tripeptide having a wound healing activity.

Another object of the invention is to provide a pharmaceutical composition for wound healing containing said tripeptide as an effective ingredient.

These objects have been achieved by the invention of L-lysyl-glycyl-L-histidine or metal complexes thereof as a promoter of fibroblast proliferation and wound healing.

DETAILED DESCRIPTION OF THE INVENTION

TGF-β and PDGF, which were hitherto considered to have a wound healing effect, are physiologically active substances having various functions of themselves and are considered to have other undesirable activities than wound healing. Therefore, a low molecular peptide having no such side effects and being specifically active in wound healing has been desired for the above purposes.

The present inventors have found, as a result of various studies, the fact that L-lysyl-glycyl-L-histidine and/or metal complexes thereof such as L-lysyl-glycyl-L-histidine: copper (II) promotes fibroblast proliferation, and this invention has now been completed.

The tripeptide and metal complexes thereof according to this invention are highly water-soluble, and they are most suitably administered in combination with a suitable water-soluble base for wound healing preferably by applying locally to an affected region. Preparations for an external use according to the invention may take the form of a water-soluble ointment, an oleaginous ointment, lotion, spray, oil, gel or the like. Representative bases may include macrogols for a water-soluble ointment, vaseline for an oleaginous ointment, vegetable oils such as olive oil, sesame oil, camellia oil and the like for an oil preparation, and carboxy vinyl polymer, sodium polyacrylate and the like for a gel preparation. The tripeptide and metal complexes thereof according to the invention can also be administered intravenously or subcutaneously in systemic administration, and nasally or transpulmonarily in the form of micronized aerosols.

The dosages are in a range of 1 to 100 mg/administration site/person/day in local administration, and 0.1 to 10 mg/kg/day in systemic administration.

The following examples are provided to illustrate the invention and are not intended to limit the invention.

EXAMPLES

Example 1

Synthesis of L-lysyl-glycyl-L-histidine

A peptide consisting of L-lysyl-glycyl-L-histidine was synthesized by way of solid-phase synthesis using an automatic peptide synthesizer (Applied Biosystems, Inc., U.S.A.). Using 0.5 mM of resin comprising styrene-divinylbenzene copolymer (molar ratio; styrene: divinylbenzene= 99:1), amino acids were connected successively toward the N-terminus of the peptide. One mM of N-(t-butoxycarbonyl)-L-Lys, N-(t-butoxycarbonyl)-Gly and N-(t-butoxycarbonyl)-L-His, respectively, were used as amino acids in the reaction. The peptides were obtained by the detachment from the solid-phase and the removal of protecting group by using 5 ml of 95% trifluoroacetic acid (TFA). The peptides obtained were purified by HPLC (available from Hitachi Corp.), then reverse-phase C-18 column (available from Vydac, Inc.) eluting with a linear gradient of acetonitrile containing 0.1% TFA.

Example 2

Determination of Fibroblast Proliferation Promoting Activity of L-lysyl-glycyl-L-histidine

Fibroblast cell strains, Balb/3T3 cells (purchased from ATCC) were inoculated into a 96-well culture plate at $5\times10^3$ cells/well, 100 µl of 10% calf serum-containing Dulbecco Modified Eagle Medium (hereinafter referred to as DME) was added and incubated at. 37 ûC for 24 hours in an incubator. Then, the culture medium was removed and the cells were washed. One hundred µl of lowered serum medium (0.2% calf serum-containing DME) Was added to the wells and incubation was continued for another 3 days. L-lysyl-glycyl-L-histidine obtained in Example 1 was added thereto at 10 µl/well and incubation was performed for 15 hours. The culture medium contains a trace amount of $Cu^{2+}$, and a part of L-lysyl-glycyl-L-histidine may form copper complexes. The 3H-thymidine was added to be 74 KBq/ml and incubation was performed for 6 hours. After completion of the incubation, the medium was removed, the cells were collected and the amount of 3H-thymidine incorporated in the cells was determined.

The results of the determination of fibroblast proliferation promoting activity of L-lysyl-glycyl-L-histidine are shown in Table 1, wherein the data show the mean and its standard deviation (4 cases per one group).

TABLE I

| Added Compound | Dose (M) | Incorporated 3H-thymidine (cpm) |
|---|---|---|
| Control | — | 1392.3 ± 348.2 |
| L-lysyl-glycyl-L-histidine | $10^{-6}$ | 1406.5 ± 470.5 |
| | $10^{-5}$ | 1371.8 ± 249.1 |
| | $10^{-4}$ | 4889.8 ± 495.1 |
| | $10^{-3}$ | 7719.5 ± 1246.8 |

From the results, it was confirmed that L-lysyl-glycyl-L-histidine has a dose-dependent cell proliferation promoting activity.

What is claimed is:

1. A tripeptide comprising an amino acid sequence L-lysyl-glycyl-L-histidine or a metal complex thereof.

2. The tripeptide according to claim 1 comprising an amino acid sequence L-lysyl-glycyl-L-histidine.

3. The tripeptide metal complex according to claim 1, wherein said metal is copper (II).

4. A pharmaceutical composition for wound healing containing an effective amount of a tripeptide comprising an amino acid sequence L-lysyl-glycyl-L-histidine or a metal complex thereof or both as an active ingredient.

5. The pharmaceutical composition for wound healing according to claim 4 wherein the tripeptide comprises an amino acid sequence L-lysyl-glycyl-L-histidine.

6. The pharmaceutical composition for wound healing according to claim 4 wherein the tripeptide metal complex comprises L-lysyl-glycyl-L-histidine: copper (II).

7. A method for promoting wound healing in a subject, comprising the step of administering to said subject a wound healing effective amount of the pharmaceutical composition according to claim 4.

8. A method of claim 7, wherein said pharmaceutical composition is administered systemically.

9. A method of claim 8, wherein said systemic administration is at a dosage of 0.1 to 10 mg/kg/day.

10. A method of claim 7, wherein said pharmaceutical composition is administered locally.

11. A method of claim 10, wherein said local administration is at a dosage of 1 to 100 mg/site of administration.

* * * * *